United States Patent [19]

Bernheim et al.

[11] Patent Number: 4,956,049
[45] Date of Patent: Sep. 11, 1990

[54] PROCESS FOR SIZING PAPER WITH ANIONIC HYDROPHOBIC SIZING AGENTS AND CATIONIC RETENTION AIDS

[75] Inventors: Michael Bernheim, Augsburg; Dieter Strasilla, Weil am Rhein, both of Fed. Rep. of Germany; Bernardo De Sousa, Riehen; Peter Rohringer, Schönenbuch, both of Switzerland

[73] Assignee: Ciba-Geigy Corporation, Ardsley, N.Y.

[21] Appl. No.: 372,217

[22] Filed: Jun. 23, 1989

Related U.S. Application Data

[63] Continuation of Ser. No. 110,896, Oct. 21, 1989, abandoned, which is a continuation of Ser. No. 760,865, Jul. 31, 1989, abandoned.

[51] Int. Cl.$^5$ ............................................. D21H 17/14
[52] U.S. Cl. .................................. 162/158; 162/164.6; 162/166; 162/168.2; 162/175; 162/179; 162/181.1
[58] Field of Search ...................... 162/158, 179, 164.3, 162/164.6, 166, 168, 175, 181.1

[56] References Cited

U.S. PATENT DOCUMENTS

| 2,448,247 | 8/1948 | Bellwood | 162/158 |
| 2,665,206 | 1/1954 | Bradley | 162/158 |
| 2,665,207 | 1/1954 | McMillan et al. | 162/158 |
| 2,692,183 | 10/1954 | Ericks | 162/158 |
| 4,127,418 | 11/1978 | Bateman | 162/158 |

FOREIGN PATENT DOCUMENTS

| 96654 | 12/1983 | European Pat. Off. | 162/179 |
| 2828384 | 1/1979 | Fed. Rep. of Germany | 162/158 |

OTHER PUBLICATIONS

Casey, *Pulp and Paper*, vol. II (1981), pp. 1574, 1577, 1602, 1603, 1604, 1914 and 1915.
The Dictionary of Paper–Fourth Edition (1980), p. 267.

*Primary Examiner*—Peter Chin
*Attorney, Agent, or Firm*—Edward McC. Roberts

[57] ABSTRACT

Sizing agents, some of which are known compounds and some of which are novel aromatic compounds which contain in the aromatic nucleus a single hydrophobic substituent containing at least 5 carbon atoms and at least one anionic group, said hydrophobic substituent being linked to the aromatic nucleus through an ester, amide, urethane or urea bridge, with the CO group of ester and amide bridges being attached to the hydrophobic radical and a methylene group being optionally present between said bridges and the aromatic nucleus, are particularly suitable, together with commercially available retention aids, for use in a process for the mass sizing of paper or cardboard or for the surface sizing of paper.

11 Claims, No Drawings

PROCESS FOR SIZING PAPER WITH ANIONIC HYDROPHOBIC SIZING AGENTS AND CATIONIC RETENTION AIDS

This application is a continuation of application Ser. No. 110,896, filed 10/21/89 abandoned, which is a continuation of application Ser. No. 760,865 filed 07/31/85, abandoned The present invention has for its object to provide the paper manufacturer with readily available sizing agents which are obtainable in simple manner and, when combined in a novel manner with conventional cationic retention aids, are able to effect good sizing in the manufacture of paper from fibre suspensions (mass sizing) as well as in the manufacture of paper with sized surface (surface sizing).

This object is achieved in the practice of this invention by using, as sizing agents for paper manufacture involving the concurrent use of conventional polymeric cationic retention aids, aromatic compounds which carry a single long chain hydrophobic substituent and at least one anionic group which is acidic or in salt form, said hydrophobic substituent being attached to the aromatic nucleus through a bridge that contains at least one carbon atom and at least two hetero atoms in the main chain.

Accordingly, the present invention relates to a process for sizing paper or cardboard, i.e. to a process for the preparation of mass sized paper or cardboard or of surface-sized paper, which process comprises using at least (A) a sizing agent consisting of an aromatic compound which contains in the aromatic nucleus a single hydrophobic substituent having at least 5 carbon atoms and at least one anionic group which is acidic or in salt form, said hydrophobic substituent being attached to the aromatic nucleus through an ester, amide, urethane or urea bridge, with the CO group of ester and amide bridges being linked to the hydrophobic radical and a methylene group being optionally present between said bridges and the aromatic nucleus, and (B) a polymeric cationic retention aid.

In the process of this invention for the mass sizing of paper or cardboard, components (A) and (B) are added, in any order or simultaneously, to aqueous cellulose-containing pulp suspensions that may also contain fillers, whereas in surface sizing the paper is impregnated with an aqueous sizing liquor which contains components (A) and (B) and dried.

Further objects of the invention are:

the aqueous compositions for carrying out the paper sizing process, which compositions contain, if the sizing agent (A) and the retention aid (B) are added separately, in any order, to the fibre suspension for mass sizing, only the sizing agent (A) which is at least partly in salt form, together with optional conventional auxiliaries, or, if the sizing agent (A) and the retention aid (B) are added simultaneously to the fibre suspension for mass sizing, or are used as sizing liquor for surface sizing paper, contain the sizing agent (A) which may be at least partially in salt form as well as the retention aid (B), together with optional conventional auxiliaries, the paper or cardboard sized by the process of the present invention, and the use of the sizing agent (A) of the indicated kind for sizing paper or cardboard.

Some of the sizing agents (A) are novel compounds which, together with the process for their preparation, likewise constitute further objects of the invention.

As salient feature, the sizing agents (A) of this invention normally contain 1 or 2 anionic groups which are usually in the form of acid carboxyl, hydroxyl or sulfo groups which are attached to the aromatic nucleus. If the sizing agents contain two acidic groups, then one of these groups is preferably a hydroxyl group. Sizing agents that contain only one acidic group are preferred. If these groups are in salt form, for example as amine, ammonium or sodium salts, they can form anions in aqueous medium at the normal pH values of fibre suspensions in paper manufacture. Under the indicated conditions, the cationic retention aids (B) are able to form cations. The ability of the sizing agents to form anions and that of the retention aids to form cations under the conditions of paper manufacture can also be termed anionic and cationic respectively. Thus the sizing agents and the retention aids can also be termed anion-liberating sizing agents and cation-liberating retention aids.

The sizing agents (A) are also characterised by the feature that they contain one single, preferably aliphatic, hydrophobic substituent containing not less than 5, in particular 5 to 22, preferably 11 to 22 and, most preferably, 16 to 20 carbon atoms. Preferred hydrophobic substituents are alkenyl or, in particular, alkyl radicals, which are usually derived from unsaturated or, preferably, saturated fatty acids or so-called fatty isocyanates. The hydrophobic substituents thus consist only of carbon and hydrogen atoms and are attached to a divalent bridge of the indicated kind.

Suitable fatty acids from which the hydrophobic substituents are derived are unsaturated or, preferably, saturated fatty acids of 6 to 22, preferably 11 to 22 and, most preferably, 16 to 20 carbon atoms. Such acids are for example capronic acid, preferably caprylic acid, lauric acid, myristic or myristoleic acid, palmitoleic acid, eleostearic acid, clupadonic acid, in particular oleic acid, elaidic acid, erucic acid, linolic acid and linoleic acid. Palmitic, stearic, oleic and behenic acid are particularly important, with palmitic and stearic acid being preferred. Also suitable are fatty alcohols and fatty amines which are derived from technical, readily accessible mixtures of the above acids. Synthetic fatty alcohols which are prepared e.g. by oxosynthesis also fall within the above definition.

The fatty isocyanates contain a long chain radical which is usually derived from a fatty acid of the indicated kind. These fatty isocyanates can be obtained from the appropriate fatty amines and phosgene. Because of its ready accessibility, octadecyl isocyanate, also called stearyl isocyanate, is particularly preferred. It is also possible to use technical mixtures of fatty isocyanates of the indicated kind.

The manner in which the hydrophobic substituent is attached to the aromatic nucleus constitutes a further feature of the sizing agent (A). As previously mentioned, these divalent bridges are ester bridges —O—CO—, amide bridges —NH—CO—, urethane bridges —NH—CO—O— or urea bridges —NH—CO—NH—, which bridges contain an oxygen atom, a nitrogen atom, an oxygen and a nitrogen atom or two nitrogen atoms in the main chain, with the terminal carbonyl group —CO— of the ester and amide bridges (in contradistinction to the carbonyl group of the urethane or urea bridges, which is not terminal) being always attached to the hydrophobic radical, whereas the oxygen atom of the ester bridge and the —NH group of the amide bridge are always attached to the aromatic nucleus of an aromatic compound employed as sizing agent. A methylene group may additionally be present between the above bridges, in particular between the ester and, preferably, the amide bridge and the aromatic nucleus. However, the bridges are preferably attached direct to the aromatic nucleus.

The nucleus of the aromatic compounds may suitably be tetrahydronaphthylene or dihydronaphthylene, preferably naphthylene and, most preferably, phenylene. These divalent aromatic radicals are unsubstituted or substituted e.g. by amino, nitro and/or halogen, preferably bromine or, most preferably, chlorine. However, unsubstituted divalent aromatic radicals are preferred.

Accordingly, component (A) of the paper sizing process of the present invention is a sizing agent of the formula

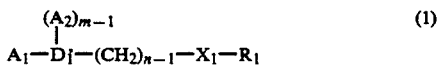

(1)

wherein

A$_1$ and A$_2$ are each independently of the other an anionic carboxyl, hydroxyl or sulfo group which is acidic or in salt form, D$_1$ is phenylene, naphthylene, dihydronaphthylene or tetrahydronaphthylene, each of which is unsubstituted or substituted by halogen, nitro, amino or hydroxyl, R$_1$ is alkyl or alkenyl, each of 5 to 22 carbon atoms, X$_1$ is a bridge of the formula —O—CO—, —NH—CO—, —NH—CO—O—, —O—CO—NH— or —NH—CO—NH—, wherein terminal —CO— groups of said bridge are attached to the alkyl or alkenyl radical R$_1$, and m and n are each independently of the other 1 or 2.

If X$_1$ is a urethane bridge, its terminal —NH— group is preferably attached to the alkyl or alkenyl radical R$_1$ owing to better accessibility of the corresponding compounds.

As the methylene group is present in particular between an ester or amide bridge, and as the aromatic nucleus is unsubstituted or substituted naphthylene or, preferably, unsubstituted or substituted phenylene, and as the compounds which carry methylene groups preferably contain only a single anionic group of the indicated kind, further preferred sizing agents are those of the formula

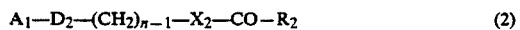

(2)

or

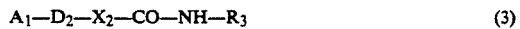

(3)

wherein

D$_2$ is phenylene or naphthylene, each unsubstituted or substituted by chlorine, bromine, nitro, amino or hydroxyl, R$_2$ is alkyl or alkenyl, each of 5 to 21 carbon atoms, R$_3$ is alkyl or alkenyl, each of 6 to 22 carbon atoms, X$_2$ is —O— or —NH— and A$_1$ and n have the given meanings.

In this connection, it should be mentioned that the radical —CO—R$_2$ in formula (2) is derived from C$_6$–C$_{22}$ fatty acids, wherein the carbonyl group of the fatty acid is included. For this reason R$_2$ is alkyl or alkenyl, each of 5 to 21 carbon atoms, in contrast to R$_3$ in formula (3), which contains from 6 to 22 carbon atoms and is derived from a C$_6$–C$_{22}$ fatty isocyanate.

The most preferred representatives of sizing agents which carry methylene groups are substituted in the aromatic nucleus and contain amide bridges and hydrophobic substituents which are preferably derived from C$_6$–C$_{22}$ fatty acids. As sizing agents of this kind it is accordingly preferred to use those of the formula

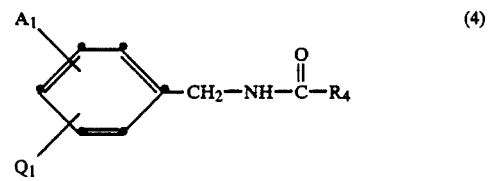

(4)

wherein Q$_1$ is chlorine, bromine, nitro or amino, R$_4$ is alkyl or alkenyl, each of 15 to 21 carbon atoms, and A$_1$ has the given meanings.

Preferably, however, the sizing agents do not carry any methylene groups of the indicated kind and are not substituted in the aromatic nucleus. In addition, they carry an anionic or acidic group of the indicated kind and may carry a hydroxyl group as second anionic or acidic group. Sizing agents of the formula

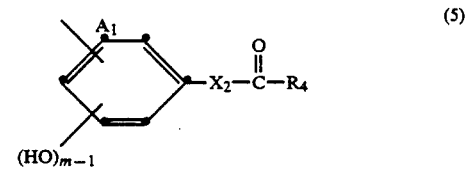

(5)

or

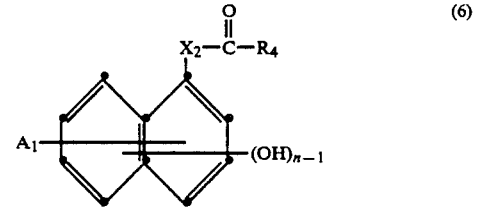

(6)

wherein A$_1$, R$_4$ X$_2$, m and n have the given meanings, are illustrative of sizing agents of this kind which contain amide or ester bridges and carry hydrophobic substituents that are preferably derived from C$_{16}$–C$_{22}$ fatty acids.

If, on the other hand, the preferred sizing agents devoid of methylene groups contain urethane or urea bridges and carry hydrophobic substituents that are preferably derived from C$_{16}$–C$_{22}$ fatty amines, but are not substituted in the aromatic nucleus, then, for example, sizing agents of the formula

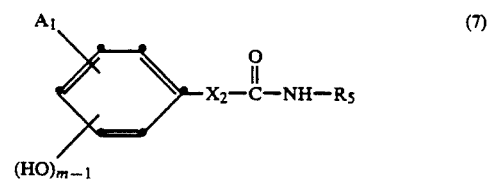

(7)

-continued or

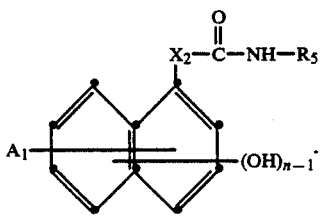 (8)

are employed, wherein R₅ is alkyl or alkenyl, each of 16 to 22 carbon atoms, and $A_1$, $X_2$, m and n have the given meanings. The sizing agents containing phenylene radicals of formula (5) or (7) are preferred to those containing naphthylene radicals of formula (6) or (8).

Sizing agents of formula (4), preferably of formula (7) and, most preferably, of formula (5), are preferred to the sizing agents of formulae (6) and (8).

Examples of specific representatives of sizing agents of formula (4) are those of formula

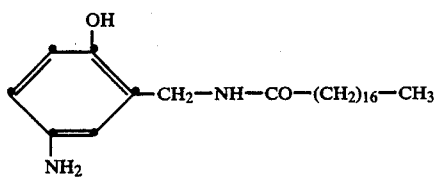 (9)

and

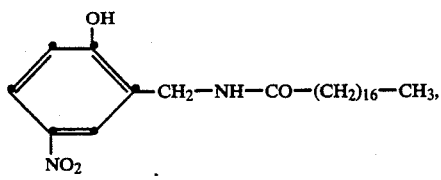 (10)

and examples of specific representatives of formula (5) are those of formula

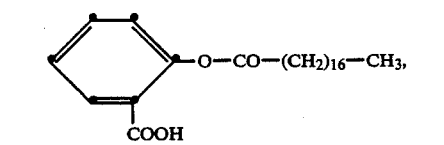 (11)

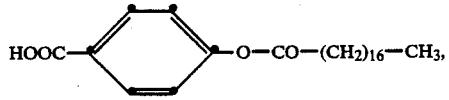 (12)

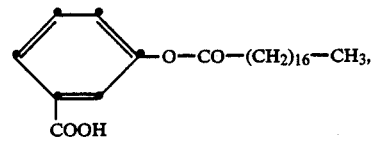 (13)

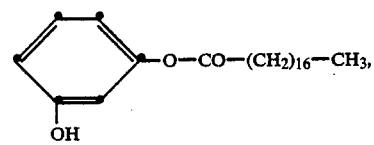 (14)

-continued

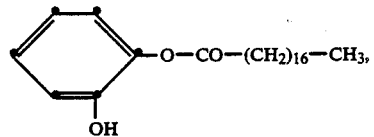 (15)

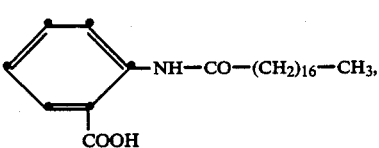 (16)

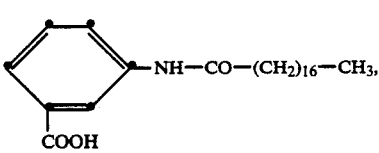 (17)

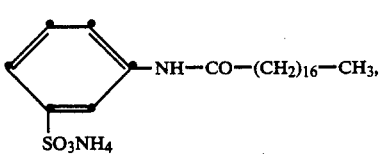 (18)

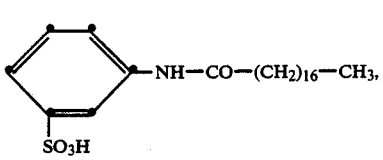 (19)

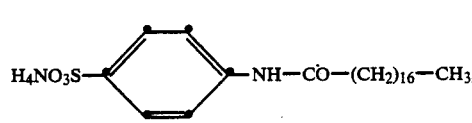 (20)

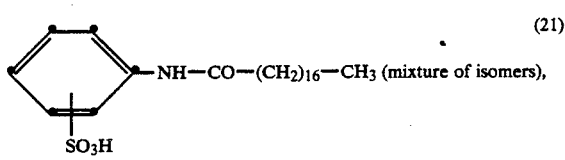 (21)

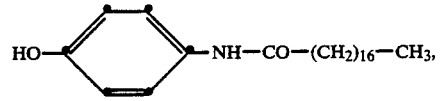 (22)

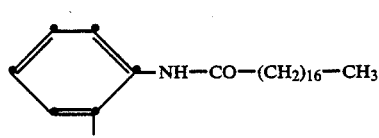 (23)

and

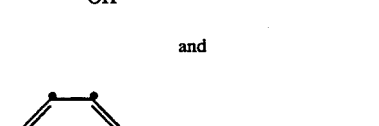 (24)

A specific representative of formula (6) is for example the sizing agent of formula

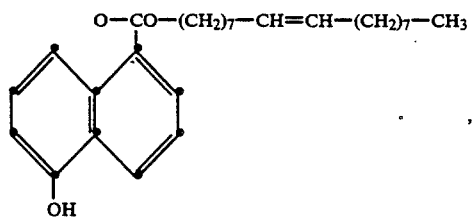 (25)

and examples of specific representatives of sizing agents of formula (7) are those of formula

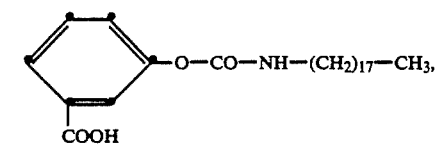 (26)

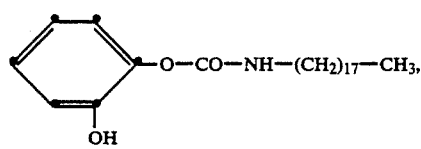 (27)

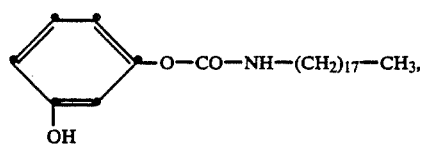 (28)

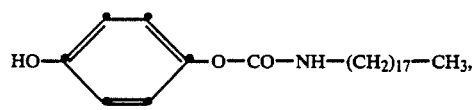 (29)

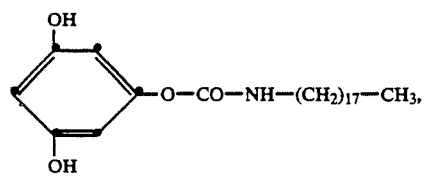 (30)

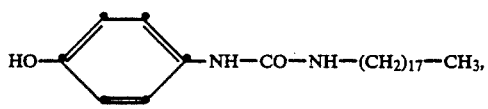 (31)

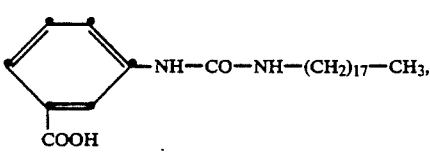 (32)

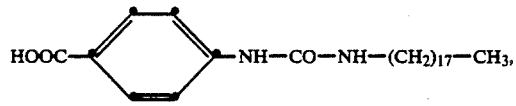 (33)

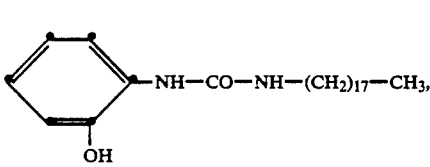 (34)

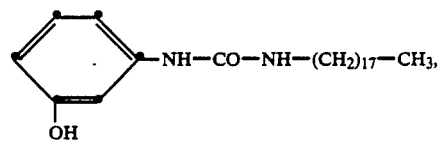 (35)

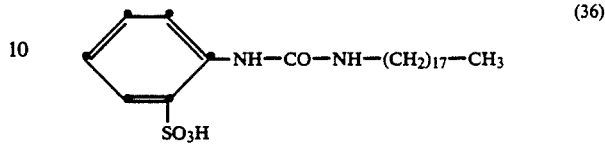 (36)

and

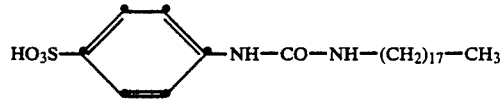 (37)

A specific representative of formula (8) is for example the sizing agent of formula

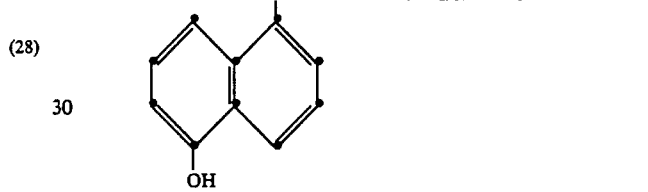 (38)

Of preeminent interest are the sizing agents of formula (23) and, in particular, of formula (15).

Before their use as component (A) in the paper sizing process of this invention, the sizing agents normally do not need to be purified, for example by recrystallisation, after their synthesis, but can be employed direct, i.e. as crude products.

Especially when adding the sizing agent (A) and the retention aid (B) separately (in any order) to the fibre suspension in the process of this invention for mass sizing paper or cardboard, it is convenient to add the sizing agent at least partly in salt form. As required, such salts can be prepared by converting the sizing agents (A), after their synthesis, wholly or partly into the corresponding salts by adding e.g. an alkylamine or alkanolamine containing a total of not more than 6 carbon atoms, e.g. trimethylamine, triethylamine, monoethanolamine or diethanolamine, preferably by adding ammonia or an alkali metal hydroxide, for example potassium hydroxide or, in particular, sodium hydroxide, normally in aqueous medium at room temperature (from about 15° to 25° C.). It is convenient to use an alkali metal hydroxide, e.g. potassium hydroxide or, preferably, sodium hydroxide, or especially ammonia, usually in the form of a dilute aqeuous solution (about 1 to 10% by weight). It is advantageous to use generally up to 2 moles, preferably from 0.1 to 1.5 moles and, most preferably, 0.9 to 1.1 moles of ammonia or alkali metal hydroxide per available acid group of the sizing agent. The sizing agents obtained in the form of their salts thus contain acid carboxyl, hydroxyl or sulfo groups which are at least partly converted into the —COO$^{\ominus}$M$^{\oplus}$, O$^{\ominus}$M$^{\oplus}$ or SO$_3^{\ominus}$M$^{\oplus}$ group, wherein M⊕ denotes the corresponding amine, ammonium or alkali metal cations.

Preferred sizing agents (A) of the indicated kind have molecular weights of about 200 to 700, preferably from about 350 to 600, and, because they contain at least one acid group of the indicated kind, have an acid number (mg of KOH/g of substance) of about 80 to 500, preferably of about 100 to 300.

As already indicated, some of the sizing agents used as component (A) in the paper sizing process of this invention are compounds which are known per se and some are novel compounds which can be prepared by methods which are known per se.

Thus, for example, sizing agents which carry methylene groups between a substituted phenylene ring and the amide bridge are novel compounds which have e.g. the formula

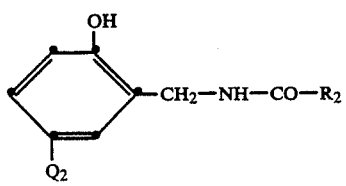

(39)

wherein $Q_2$ is nitro or amino and $R_2$ is alkyl or alkenyl, each of 5 to 21, preferably of 15 to 21, carbon atoms, and, in particular, the formula (9) or (10), or salts thereof, for example the ammonium, amine or sodium salts thereof. The process for the preparation of the compounds of formula (39) comprises reacting a methylolated fatty acid amide of the formula

$R_2$—CO—NH—CH$_2$OH     (40)

wherein $R_2$ has the given meanings, with p-amino or p-nitrophenol, in a manner known per se, optionally with an excess of p-amino or p-nitrophenol, but preferably in about equimolar amounts.

o- and p-Stearoyloxybenzoic acid, i.e. compounds of formula (5), wherein $A_1$ is carboxyl in ortho- or para-position, $R_4$ is $C_{17}$alkyl, $X_2$ is —O— and m is 1; as well as 3-stearoyloxy- or 3-lauroyloxynaphthalen-2-monocarboxylic acid, i.e. compounds of formula (6), wherein $A_1$ is carboxyl, $R_4$ is $C_{17}$alkyl or $C_{11}$alkyl, $X_2$ is —O— and m is 1, with $A_1$ being in the 2-position and —$X_2$CO—$R_4$ being in the 3-position, are disclosed e.g. as water repellants for textiles in U.S. Pat. No. 2,448,247. This reference, however, makes no mention of the corresponding m- and 1,5-isomers. Further, European Patent Application No. 60,092 discloses compounds of formula (5), wherein $A_1$ is hydroxyl in the para-position, $R_4$ is $C_1$–$C_{20}$alkyl or $C_1$–$C_{20}$alkenyl, $X_2$ is —O— and m is 1, in particular hydroquinone monostearate, as active ingredient of cosmetic compositions for depigmenting the skin. This reference makes no mention of corresponding isomers, i.e. the m- and o-isomers. Finally, German "Offenlegungsschrift" No. 2,260,703 discloses anionic compounds of formula (5) or (6), wherein $A_1$ in any position is SO$_3$Na or SO$_3$NH$_4$, $R_4$ is $C_7$–$C_{21}$alkyl or $C_7$–$C_{21}$alkenyl, $X_2$ is —O— and m is 2 or preferably 1, as dyeing assistants. Accordingly, those compounds, or salts thereof, are novel per se which correspond e.g. to the formula

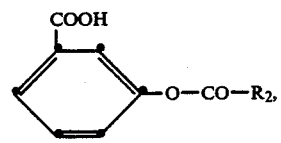

(41)

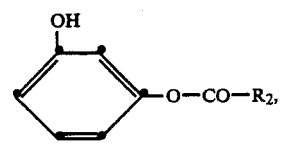

(42)

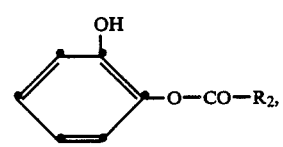

(43)

or

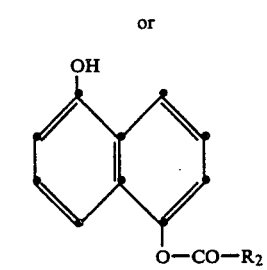

(44)

wherein $R_2$, or alkenyl, each of 5 to 21, preferably 15 to 21, carbon atoms, and, in particular, to the formulae (13), (14), (15) or (25). The process for the preparation of these compounds comprises reacting a fatty acid of the formula

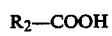

$R_2$—COOH     (45)

wherein $R_2$ has the given meanings, or a halide thereof, preferably the chloride, with 3-hydroxybenzoic acid, resorcinol, pyrocatechol or 1,5-dihydroxynaphthalene, in a manner known per se, optionally with an excess of the cited aromatic starting materials, in particular with an excess of resorcinol, pyrocatechol or 1,5-dihydroxynapohthalene, but preferably in about equimolar amounts.

Compounds of formula (5), wherein $A_1$ in any position is $C_{10}$–$C_{30}$alkyl or $C_{10}$–$C_{30}$alkenyl, $X_2$ is —NH— and m is 1, are disclosed in U.S. Pat. No. 3,773,663 as coating agents for asbestos in lubricatring greases. Further, compounds of formula (5), wherein $A_1$ in any position is a sulfo group, $R_4$ is alkyl of not less than 6 carbon atoms, $X_2$ is —NH— and m is 1, are disclosed in German "Auslegeschrift" No. 1,140,077 as adhesives for emulsion and auxiliary layers on acetyl cellulose films. Finally, U.S. Pat. No. 4,002,701 discloses N-alkanoyl-p-aminophenol as stabiliser for polyethylene and polyvinyl resins, i.e. compounds of formula (5), wherein $A_1$ in the para-position is hydroxyl, $R_4$ is $C_6$–$C_{23}$alkyl, $X_2$ is —NH— and m is 1. This reference, however, makes no mention of the o- and p-isomers, for example N-alkanoyl-o-aminophenol or N-alkanoyl-m-aminophenol. This applies also to U.S. Pat. No. 4,320,209, which discloses N-stearoyl-p-aminophenol as agent for accelerating the crystallisation of polymers, to U.S. Pat. No. 3,288,885, which discloses N—$C_2$—$C_{20}$acyl-p-aminophenol as stabiliser for polymer compositions, and to French Patent No. 2,115,676, which discloses N-stearoyl-p-aminophenol or N-lauroyl-p-aminohenol as additive for polyamide moulding compositions.

Accordingly, those compounds, or salts thereof, are novel per se which have e.g. the formula

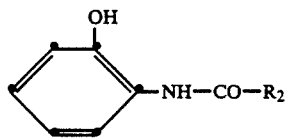  (46)

or

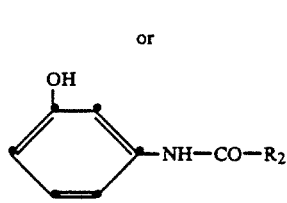  (47)

wherein $R_2$ is alkyl or alkenyl, each of 5 to 21, preferably 15 to 21, carbon atoms, and especially the formula (23) or (24). The process for the preparation of these compounds comprises reacting a fatty acid of formula (45), or a halide thereof, preferably the chloride, with o- or p-aminophenol, in a manner known per se, optionally with an excess thereof, but preferably in about equimolar amounts.

The sizing agents which contain urethane bridges are also in general novel compounds per se, or salts thereof, which have preferably the formula (7), wherein $X_2$ is —O—. Such compounds, or salts thereof, are in particular those of the formula

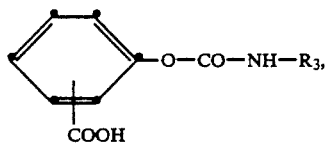  (48)

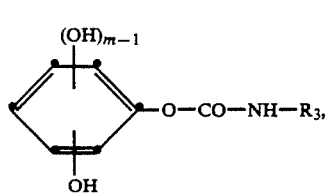  (49)

or

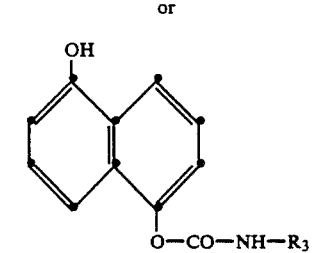  (50)

wherein $R_3$ is alkyl or alkenyl, each of 6 to 22, preferably 16 to 22, carbon atoms, and m is 1 or 2, and, in particular, those of the formulae (26) to (30) or (38). The process for the preparation of these compounds comprises reacting an alkyl isocyanate or alkenyl isocyanate of the formula $$R_3-N=C=O \quad (51)$$

wherein $R_3$ has the given meanings, with 2-, 3- or 4-hydroxybenzoic acid, pyrocatechol, resorcinol, hydroquinone, phloroglucinol, hydroxyquinone, pyrogallol or 1,5-dihydroxynaphthalene, in a manner known per se, optionally with an excess of aromatic starting material, preferably one containing 2 or 3 hydroxyl groups, but preferably in about equimolar amounts. The isocyanate of formula (51) is normally obtainable from the corresponding fatty amines and phosgene and is commercially available.

Compounds of formula (7) containing urethane bridges, wherein $A_1$ is hydroxyl in the para-position, $R_2$ is e.g. n-octadecyl, $X_2$ is —NH— and m is 1, are disclosed as antioxidants for light petroleum in U.S. Pat. No. 2,683,083, but no reference is made therein to the corresponding o- and m-isomers.

Accordingly, those compounds, or salts thereof, are novel per se which have e.g. the formula

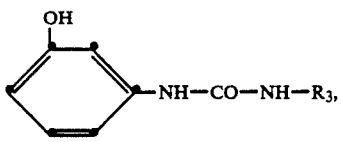  (52)

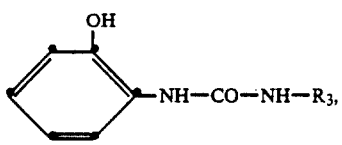  (53)

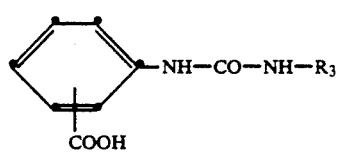  (54)

or

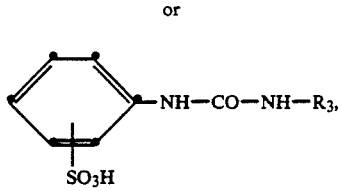  (55)

wherein $R_3$ is alkyl or alkenyl, each of 6 to 22, preferably 16 to 22, carbon atoms, and, in particular, which have the formulae (32) to (37). The process for the preparation of these compounds comprises reacting an alkyl isocyanate or alkenyl isocyanate of the formula (51) with 2- or 3-aminophenol, 2-, 3- or 4-aminobenzoic acid or aniline-2-, -3- or -4-sulfonic acid, in a manner known per se, optionally with an excess of the specified aromatic starting materials, but preferably about equimolar amounts.

In the paper sizing process of this invention, a polymeric cationic retention agent (B), which normally has a molecular weight of about at least 1000, preferably about 2000 to 2 000 000, is always used in addition to the novel anionic or acid sizing agent (A).

Retention aids having a molecular weight in the range from 10 000 to 100,000 are particularly preferred. In principle, any commercially available retention aid is suitable for use in the process of this invention. Examples of conventional retention aids (B) which are particularly suitable for use, together with the sizing agent (A), in the process of this invention, are polyalkylenimines, adducts of epihalohydrin with reaction products of polyalkylenepolyamines and aliphatic dicarboxylic acids; adducts of epihalohydrin with reaction products of polyalkylenepolyamines, dicyandiamide and organic dicarboxylic acids which are free or esterified with alkanols; reaction products of dicyandiamide, formaldehyde, ammonium salts of strong inorganic acids and alkylenediamines or polyalkylenepolyamines; cationically modified starches or carbohydrates from carob bean gum or guar gum; copolymers based on polyamide amines and reaction products of epihalohydrins and polymerised diallyl amines.

Preferred adducts of epichlorohydrin with reaction products of polyalkylenepolyamines and aliphatic dicarboxylic acids are described e.g. in British Patent No. 865,727; adducts of epichlorohydrin with reaction products of dicyandiamide and diethylenetriamine or triethylenetetramine are described e.g. in German "Offenlegungsschrift" No. 2,710,061 and in British Patent No. 1,125,486; adducts of epichlorohydrin with reaction products of diethylenetriamine, dicyandiamide and dicarboxylic acids which are free or preferably esterified with lower alkanols, in particular dimethyl adipate, are described e.g. in British Patent No. 1,125,486, and reaction products of dicyandiamide, formaldehyde, ammonium salts of strong inorganic acids and of ethylenediamine or triethylenetetraamine, are described e.g. in U.S. Pat. No. 3,491,064. Preferred cationically modified starches or carbohydrates from carob bean gum or guar gum are e.g. adducts of alkylene oxide with these starches or carbohydrates in which the alkylene oxide employed contains 2 or 3 carbon atoms in the alkylene moiety and quaternary ammonium groups. Copolymers based on polyamide amines have molecular weights of $10^3$ to $10^5$, preferably of $10^3$ to $10^4$, and are obtainable e.g. from aliphatic saturated dicarboxylic acids containing 2 to 10 carbon atoms, preferably 3 to 6 carbon atoms, preferably adipic acid, and polyalkylenepolyamines, e.g. polypropylenepolyamine and polyethylenepolyamine, preferably dimethylaminohydroxypropyl diethylenetriamine. They are described e.g. in the CTFA Cosmetic Ingredient Dictionary, 3rd edition 1982 (CFTA=Cosmetic Toiletry and Fragrance Association). Reaction products of epihalohydrins and polymerised diallyl amines preferably have molecular weights of 1000 to 2000 and are described e.g. in U.S. Pat. Nos. 3,700,623 and 4,279,794.

Typical examples of preferred retention aids (B) which are used together with the sizing agents (A) in the paper sizing process of this invention are a maize or potato starch modified with a propylene oxide which contains quaternary ammonium groups, a 25% suspension of which in distilled water at 20° C. has a pH of 4.2 to 4.6, a polyethylenimine having a molecular weight of 10,000 to 100,000, an adduct of epichlorohydrin with a reaction product of triethylenetetraamine and dicyandiamide, an adduct of epichlorohydrin with a reaction product of diethylenetriamine, dicyandiamide and dimethyl adipate, a reaction product of diacyandiamide, formaldehyde, ammonium chloride and ethylenediamine, an adduct of epichlorohydrin with a poly-N-methyl diallyl amine, and a copolymer of adipic acid and dimethylaminohydroxypropyl diethylenetriamine.

In the process of this invention for the mass sizing of paper or cardboard, 0.02 to 3, preferably 0.05 to 3, in particular 0.1 to 0.8 percent by weight of the sizing agent (A), and 0.02 to 3, preferably 0.05 to 3, in particular 0.1 to 0.4 percent by weight of the retention aid (B) will normally be used, said amounts both being expressed as solids in (A) and (B) and based on the solids content of the fibre suspension. An amount of 0.02 to about 0.05 percent by weight of the sizing agent (A) and of the retention aid (B) suffices only for the size press control which is not ascertainable by means of conventional sizing tests (q.v. for example the article "Control and understanding of size press pickup" by D. R. Dill in TAPPI Journal Vol. 57, No. 1, of January 1974, pp. 97–100) (TAPPI=Proceedings of the Technical Association of the Pulp and Paper Industry). The fibre suspension to which the the sizing agent (A) and the retention aid (B) are added normally has a solids content of 0.1 to 5, preferably 0.3 to 3, most preferably 0.3 to 1 percent by weight, and a Schopper-Riegler freeness of about 10° to 60°, in particular 20° to 60°, preferably 20° to 45° and, most preferably, 25° to 35°. The suspension usually contains pulp, especially pulp obtained from coniferous wood, e.g. pinewood, or from hardwood, i.e. deciduous wood, e.g. beechwood, which pulp is prepared by conventional methods, e.g. by the sulfite process or, in particular, the sulfate process. In addition, the fibre suspension may contain groundwood. The fibre suspension can also contain alum containing waste paper. Also suitable are pulp suspensions which are prepared by the CMP or CTMP process (chemimechanical and chemithermomechanical pulping processes, q.v. for example the article "Developments in refiner mechanical pulping" by S. A. Collicut and co-workers in TAPPI, Vol. 64, No. 6, of June 1981, pp. 57–61).

The fibre suspension can additionally contain organic or mineral fillers. Suitable organic fillers are e.g. synthetic pigments, for example polycondensates of urea or melamine and formaldehyde which have large specific surface areas, are in highly disperse form and are described e.g. in British Patent Nos. 1,043,437 and 1,318,244, or mineral fillers such as montmorillonite, titanium dioxide, calcium sulfate and, in particular talcum, kaolin and/or chalk (calcium carbonate). The fibre suspensions contain as a rule 0 to 40, preferably 5 to 25 and, most preferably, 15 to 20 percent by weight of the fillers of the indicated kind expressed as solids, based on the solids content of the fibre suspension.

The pH of the fibre suspension can vary within a wide range, suitable values being e.g from 3.5 to about 10.

If, for example, calcium carbonate is added, alkaline fibre suspensions with a pH of about 7 to 9, preferably 7.5 to 8.5, are obtained. In the absence of calcium carbonate, it is possible to obtain acid fibre suspensions with a pH of 3.5 to 7, preferably 5 to 7 and, most preferably, 5 to 6, by adding an acid, e.g. sulfuric acid or formic acid or, in particular, a latent acid sulfate such as aluminium sulfate (alum).

Fibre suspensions which contain no filler can have a wide pH range from e.g. 3.5 to 10. Fibre suspensions are preferred which have a pH of about 7 to 9, if desired by adding chalk, and are advantageous to the extent that possible corrosion in the sensitive paper machines is ruled out. In addition the storage stability of paper or cardboard which has been sized at pH values of 7 to 9 of the fibre suspension is markedly superior to that of paper or cardboard sized at pH values of 3.5 to 7.

The fibre suspensions can also contain additives, e.g. starch or its degradation products, which increase the fibre/fibre bond or fibre/filler bond.

It is also possible to add high molecular weight polymers of the acrylic series, e.g. polyacrylamides, with molecular weights of over 1 000 000 to the fibre suspensions as auxiliaries for retaining pulp fibre microparticles. Minimal amounts of about 0.005 to 0.02 percent by weight, expressed as solids in the polymer and based on the solids content of the fibre suspensions, suffice for this purpose.

The fibre suspension is further processed to paper or cardboard in the mass sizing process of this invention in a manner known per se on sheet formers or, preferably, continuously in paper machines of conventional construction. After drying at about 100° to 140° C. for about ½ minute to 10 minutes, paper having a variable weight per unit area of e.g. 50 to 200 g/m² is obtained.

For surface sizing paper by the process of this invention, the sizing liquor containing components (A) and (B) is applied to the paper by spraying, preferably by padding, normally at room temperature (15°–25° C.). The impregnated paper is then dried in the temperature range from 60° to 140° C., preferably from 90° to 110° C., for 0.1 to 10 minutes, preferably from 2 to 6 minutes. After drying, the resultant paper has a surface coating of sizing and retention aid of 5 to 150 mg/m², preferably from 60 to 120 mg/m².

The paper to be sized by the process of this invention is paper of any kind with any weight per unit area, for example paper and cardboard of bleached and unbleached sulfite or sulfate cellulose.

As mentioned at the outset, the aqueous composition for carrying out the paper sizing process of this invention contains the sizing agent (A), in addition to optional customary auxiliaries, provided the sizing agent and the retention aid (B) are added separately to the fibre suspension during the mass sizing. In this case, the composition contains the sizing agent entirely or, preferably, partly in salt form (obtained by concurrently using e.g. ammonia, an alkylamine or alkanolamine or an alkali metal hydroxide of the indicated kind in the ratios stated above). In general, such compositions contain 5 to 30 percent by weight, preferably 5 to 20 percent by weight, of the sizing agent which is at least partly in salt form expressed as solids, based on the weight of the aqueous composition.

On the other hand, if the sizing agent (A) and the retention aid (B) are added simultaneously to the fibre suspension in the mass sizing, the aqueous composition contains, in addition to the optional customary auxiliaries, (A) 2 to 40 percent by weight, preferably 5 to 30 percent by weight, and, most preferably, 5 to 10 percent by weight of sizing agent (calculated as solid), based on the total weight of the aqueous composition, which sizing agent is optionally in salt form, and (B) 0.1 to 20 percent by weight, preferably 0.5 to 10 percent by weight, most preferably 3 to 8 percent by weight of retention aid (calculated as solid), based on the total weight of the aqueous composition.

The aqueous compositions of the indicated kind may contain surface-active compounds as customary auxiliaries, e.g. dispersants or also emulsifiers and/or water-soluble organic solvents. Examples of suitable dispersants and emulsifiers are conventional ligninsulfonates, ligninncarboxylates, carboxymethyl cellulose, adducts of ethylene oxide and alkyl phenols, fatty amines, fatty alcohols or fatty acids, fatty acid esters of polyhydric alcohols, substituted benzimidazoles, or condensates of formaldehyde and aromatic sulfonic acids preferably naphthalinesulfonic acids. Further surface-active compounds are preferably anionic surfactants, in particular sulfate surfactants, e.g. diethanolamine lauryl sulfate, sodium lauryl sulfate or ethoxylated lauryl sulfates. Possible water-soluble organic solvents are aliphatic ethers of 1 to 10 carbon atoms, e.g. dioxan, ethylene glycol n-butyl ether or diethylene glycol monobutyl ether, or alcohols of 1 to 4 carbon atoms, e.g. isopropanol, ethanol or methanol.

If the aqueous compositions contain auxiliaries of the indicated kind, the ratio of component (A) to auxiliaries in the compositions is 1:0.02 to 1:0.3, preferably 1:0.05 to 1:0.1, based on the solids content of the sizing agent and the auxiliaries.

The compositions are prepared in conventional manner by stirring the sizing agent (A) together with the retention aid (B), or the sizing agent (A), usually partly in salt form, by itself either in the melt state or preferably in the solid state, in particular in powder form, normally in the presence of glass beads and, if necessary, of an emulsifier (if the sizing agent is in the melt state) or a dispersant (if the sizing agent is in powder form), at a maximum temperature of 90° C., preferably of about 50° to 85° C. if emulsions are prepared, and preferably at about 15° to 25° C. if dispersions are prepared, to give storage stable, homogeneous emulsions or, preferably, dispersions which can be further diluted. As the sizing agents together with the retention aids, or the sizing agents which are entirely or at least partly in salt form, are usually self-dispersing or self-emulsifying, the use of dispersants or emulsifiers is in general not absolutely necessary. This also applies to the optional use of solvents and/or surfactants, which are employed only if the storage stability of the dispersions or emulsions is insufficient.

For surface sizing paper, the requisite sizing liquor is prepared by diluting the emulsions or dispersions referred to above with water, which emulsions or dispersions contain the sizing agent (A) as well as the retention aid (B). The emulsions or dispersions are diluted such that the sizing liquor obtained contains (A) 0.02 to 0.4, preferably 0.05 to 3 and, most preferably, 0.05 to 1 percent by weight of sizing agent (calculated as solid), based on the total weight of said sizing liquor, said sizing agent being optionally in salt form, and (B) 0.01 to 0.2, preferably 0.05 to 0.1 and, most preferably, 0.3 to 0.8 percent by weight of retention aid (calculated as solid), based on the total weight of the aqueous sizing liquor.

An advantage of the process of this invention is that, for mass sizing, fibre suspensions of widely differing kind can be processed with relatively small amounts of sizing agent and retention aid, in simple manner, to give paper which has good sizing properties (ink flotation time and, in particular, water absorption according to Cobb). This applies also to surface sizing, in which the good sizing effects are obtained with small coating amounts of sizing agent and retention aid. In particular, the small coating amounts permit a rapid mode of operation, so that good surface sizing effects are obtained in the drying temperature ranges from e.g. 90° to 110° C. over about 20 to 40 seconds. The paper which is mass sized by the process of this invention has good mechanical properties, i.e. good strength, especially good tear strength. A good reproducibility of the process is ensured in mass sizing as well as surface sizing. In particular, it is possible in mass sizing to process fibre suspensions which contain groundwood or waste paper. The compatibility of the sizing agent employed in the process of the invention with different fillers, e.g. kaolin, and also with other ingredients, e.g. alum, in an acid

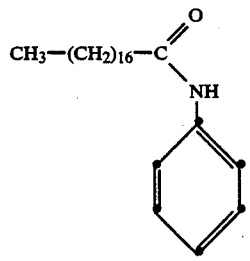

as a brownish floury powder. Melting point: 88°-89° C.

Example I, Step 2

36.0 parts (0.1 mole) of the stearanilide obtained as intermediate in step 1 are dissolved in 200 parts of chloroform and the solution is warmed to 30° C. To this solution are added 6.65 parts (0.1 mole) of chlorosulfonic acid in an inert nitrogen atmosphere over 10 minutes, whereupon the temperature of the reaction mixture rises to 45° C. and the hydrochloric acid generated by the reaction is removed from the reaction mixture. The reaction mixture is then stirred at 30° C. for 1 hour, then heated to reflux temperature of c. 63° C. and stirred at this temperature for 3 hours. The solvent is subsequently removed by vacuum distillation at 40° C. and the residue is dried, affording 50 parts of the mixture of isomers of formula (21) as a light brown wax. Melting point: 50°-60° C. (sintering temperature). Acid number: 138.

Example J 54.6 parts (0.5 mole) of p-aminophenol are heated to 50° C. in 200 parts of pyridine. To this solution are added 151 parts (0.5 mole) of stearyl chloride as a warm melt of 40° C. The temperature of the reaction mixture rises to 65° C. to form a suspension which is stirred for 4 hours at 50° C. The reaction mixture is heated further to 90° C. and, with efficient stiring, is added to 4000 parts of deionised water. The dark brown suspension is filtered and the filter product is washed with 300 parts of water and vacuum dried at 40° C., affording 147 parts of the compound of formula (22) as a pale violet powder. Melting point: 120°-122° C. Acid number: 144.

PREPARATION OF NOVEL COMPOUNDS AS SIZING AGENTS

Example 1

The procedure of Example A is repeated, using 13.8 parts (0.1 mole) of 3-hydroxybenzoic acid instead of 13.8 parts of salicylic acid, to give 36.3 parts of the compound of formula (13) as a white powder which can be recrystallised from chloroform for analysis. Melting point: 87°-91° C. Acid number: 139.

Example 2

29.5 parts (0.1 mole) of octadecyl isocyanate are added at room temperature to a suspension of 13.7 parts (0.1 mole) of 3-aminobenzoic acid in 400 parts of toluene and the mixture is heated to reflux temperature of about 111° C. The reaction mixture is kept for 1 hour at this temperature, then the solvent is removed by vacuum distillation and the residue is dried, affording 41 parts of the compound of formula (32) as an ochre powder which can be recrystallised from dioxane for analysis. Melting point: 266° C. (with decomposition). Acid number: 132.

Example 3

29.5 parts (0.1 mole) of octadecyl isocyanate are added at 20° C. over 10 minutes to a suspension of 13.8 parts (0.1 mole) of 3-hydroxybenzoic acid and 0.2 part of 1,4-diazabicyclo[2,2,2]octane (catalyst). The reaction mixture is heated to reflux temperature of c. 111° C. and kept for 5 hours at this temperature, a clear solution forming after about 4 hours. The solvent is then removed by vacuum distillation, affording 40.8 parts of the compound of formula (26) as a white powder, which can be recrystallised from a mixture of acetone/hexane for analysis. Melting point: 112°-122° C. Acid number: 116.

Example 4

The procedure of Example 3 is repeated, using 13.8 parts (0.1 mole) of 4-hydroxybenzoic acid instead of 13.8 parts of 3-hydroxybenzoic acid to give 42.3 parts of the compound of formula (33) as a white powder which can be recrystallised from dioxane for analysis. Melting point: 177°-183° C. Acid number: 119.

Example 5

27.5 parts (0.25 mole) of resorcinol and 8.7 parts (0.11 mole) of pyridine are dissolved at 50° C. in 100 parts of tetrahydrofuran. To this solution is added a solution of 30.3 parts (0.1 mole) of stearyl chloride in 50 parts of tetrahydrofuran at 50° C. over 30 minutes. The reaction mixture is heated to reflux temperature of about 67° C., stirred at this temperature for 4 hours, and then cooled to 25° C. Then 250 parts of an aqueous 0.5N hydrochloric acid solution are added to the reaction mixture, whereupon the product precipitates. The precipitate is isolated by filtration, washed with 500 parts of water of 60° C., and vacuum dried at 60° C., affording 33.5 parts of the compound of formula (14) as a white powder. Melting point: 52°-57° C. Acid number: 147.

Example 6

58.6 parts (0.2 mole) of stearic acid and 22.0 parts (0.2 mole) of resorcinol are heated to 120° C. To the resultant clear melt is added 0.2 part of 96% sulfuric acid and the mixture is heated to 160° C. The water of reaction is expelled in a stream of nitrogen. The reaction mixture is stirred for altogether 2 hours at 160° C. and then cooled to 20° C., affording 74 parts of a crude product in the form of an orange powder which contains the compound of the formula (14) as indicated in Example 5. Melting point: 73°-82° C. Acid nummber: 143.

Example 7

The procedure of Example 5 is repeated, using 27.5 parts (0.25 mole) of pyrocatechol instead of 27.5 parts of resorcinol, to give 36.4 parts of the compound of formula (15) as a white powder. Melting point: 62°-66° C. Acid number: 152.

Example 8

22.0 parts (0.2 mole) of pyrocatechol and 1.1 parts of triethylamine are dissolved in 100 parts of tetrahydrofuran and the solution is heated to 60° C. Then 59.1 parts (0.2 mole) of stearyl isocyanate are added to the above solution at this temperature over 20 minutes. The reaction mixture is then stirred for 6 hours at 60° C. The solvent is removed by vacuum distillation at 40° C. and the residue is dried, affording 79.0 parts of the compound of formula (27) as a dark brown powder. Melting point: 73°–78° C. Acid number: 142.

Example 9

The procedure of Example 8 is repeated, using 22.0 parts (0.2 mole) of resorcinol instead of 22.0 parts of pyrocatechol, to give 78.2 parts of the compound of formula (28) as a light brown powder. Melting point: 83°–86° C. Acid number: 140.

Example 10:

A solution of 32.8 parts (0.3 mole) of 2-aminophenol in 250 ml of tetrahydrofuran is added over 30 minutes at 50° C. to a solution of 90.5 parts (0.3 mole) of octadecyl isocyanate in 200 parts of tetrahydrofuran. The reaction mixture is then stirred for 16 hours at 50° C. to give a pale brown suspension. This suspension is cooled to 5° C. and filtered. The filter product is vacuum dried at 40° C., affording 30 parts of the compound of formula (34) as a beige powder, which can be recrystallised from ethanol for analysis. Melting point: 90°–93° C. Acid number: 139.

Example 11

The procedure of Example 10 is repeated, using 32.8 parts (0.3 mole) of 3-aminophenol instead of 32.8 parts of 2-aminophenol, to give 96 parts of the compound of formula (35) as a yellowish powder, which can be recrystallised from ethanol for analysis. Melting point: 108°–111° C. Acid number: 138.

Example 12

29.6 parts (0.1 mole) of stearyl isocyanate are added at 70° C. over 20 minutes to a solution of 17.3 parts (0.1 mole) of aniline-2-sulfonic acid in 100 parts of pyridine. The clear solution so obtained is heated to 80° C. and stirred for 5 hours at this temperature. After the addition of 110 parts of a 30% aqueous solution of hydrochloric acid, the reaction mixture is heated further to 100° C. Then 400 parts of deionised water are added to the reaction mixture, and the resultant white suspension is cooled to 20° C. and filtered. The filter product is washed with 300 parts of deionised water and vacuum dried at 40° C., affording 35.2 parts of the compound of formula (36) as a pale grey powder. melting point: 71°–73° C. Acid number: 129.

Example 13:

The procedure of Example 12 is repeated, using 17.3 parts (0.1 mole) of aniline-4-sulfonic acid instead of 17.3 parts of aniline-3-sulfonic acid, to give 43.5 parts of the compound of formula (37) as a pink wax-like product. Melting point: about 65° C. (sintering temperature). Acid number: 122.

Example 14:

17.5 parts (0.16 mole) of 4-aminophenol are dissolved at 0° C. in 400 parts of 96% sulfuric acid and then 50.2 parts (0.16 mole) of N-hydroxymethyl stearamide are added, in portions, at this temperature over 4 hours. The reaction mixture is stirred for 48 hours at 20° C. and then poured onto ice. The resultant suspension is filtered and the filter product is vacuum dried at 40° C., affording 41 parts of the compound of formula (9) as a grey powder which is recrystallised from ethanol for analysis. Melting point: 150°–160° C. Acid number: 145.

Example 15

The procedure of Example 14 is repeated, using 22.6 parts (0.16 mole) of 4-nitrophenol instead of 17.5 parts of 4-aminophenol, to give 40 parts of the compound of formula (10) as a grey powder, which can be recrystallised from a mixture of ethanol/acetone for analysis. Melting point: 112°–114° C. Acid number: 136.

Example 16:

A solution of 44.0 parts (0.4 mole) of hydroquinone, 29.5 parts (0.1 mole) of octadecyl isocyanate and 0.12 part of 1,4-diazabicyclo[2,2,2]octane (catalyst) in 200 parts of toluene is heated to reflux temperature of about 111° C. and stirred at this temperature for 6 hours. The reaction mixture is then cooled to 20° C. and the product precipitates. The precipitate is isolated by filtration, washed with 300 parts of water of 60° C. and vacuum dried, affording 35.5 parts of the compound of formula (29) as a white powder. Melting point: 84°–87° C. Acid number: 135.

Example 17

14.5 parts (0.14 mole) of triethylamine and then a solution of 41.4 parts (0.14 mole) of octadecyl isocyanate in 50 parts of toluene are added at 20° C. to a solution of 17.7 parts (0.14 mole) of pyragallol in 100 parts of toluene and 150 parts of dimethylsulfoxide. The reaction mixture is warmed to 45° C., stirred for 2 hours at this temperature and finally added to 500 parts of an aqueous 2N hydrochloric acid solution. The precipitated product is isolated by filtration, washed with water and vacuum dried, affording 37 parts of the compound of formula (30) as a slightly yellowish powder which can be recrystallised from ethanol for analysis. Melting point: 83°–85° C. Acid number: 261.

Example 18

A solution of 53.2 parts (0.18 mole) of octadecyl isocyanate in 50 ml of toluene and then 18.2 parts (0.18 mole) of triethylamine are added at 20° C., over 20 minutes, to a suspension of 28.8 parts (0.18 mole) of 1,5-dihydroxynaphthalene in 200 parts of toluene. The reaction mixture is heated to reflux temperature of about 111° C. and stirred for 16 hours at this temperature. The resultant clear reaction solution is then cooled to 20° C. and the product precipitates. The precipitate is isolated by filtration, washed with an aqueous 1N hydrochloric acid solution and then with water, and finally vacuum dried, affording 63 parts of the compound of formula (38) as a pale brown powder which can be recrystallised from chlorobenzene for analysis. Melting point: 153°–156° C. Acid number: 122.

Example 19

To a suspension of 32 parts (0.2 mole) of 1,5-dihydroxynaphthalene in 200 parts of toluene are added, at room temperature, first 16.1 parts (0.2 mole) of pyridine, and then, over 40 minutes, a solution of 60.2 parts (0.2 mole) of oleyl chloride in 50 ml of toluene. The reaction mixture is heated to reflux temperature of about 111° C. and then stirred at this temperature for 16 hours. The solvent is subsequently removed by vacuum distillation. The distillation residue is dissolved in 250 parts of chloroform and washed with 100 parts of an aqueous 1N hydrochloric solution and then with 100 parts of water. The chloroform solution is dried over magnesium sulfate and evaporated to dryness under vacuum, affording 82 parts of the compound of formula (25) as a viscous product. Acid number: 129.

Example 20

The procedure of Example J is repeated, using 54.6 parts (0.5 mole) of o-aminophenol instead of 54.6 parts of p-aminophenol, to give 182 parts of the compound of formula (23) as a pale beige powder. Melting point: 75°–77° C. Acid number: 142.

Example 21

The procedure of Example J is repeated, using 54.6 parts (0.5 mole) of m-aminophenol instead of 54.6 parts of p-aminophenol, to give 178 parts of the compound of formula (24) as a pale beige powder. Melting point: 102°–104°. Acid number: 140.

Example 22

22.0 parts (0.2 mole) of pyrocatechol are fused at 110° C. To this melt are added 60.5 parts (0.2 mole) of stearyl chloride over about 30 minutes such that the temperature does not exceed 120° C. The vigorous evolution of hydrogen chloride is annulled by introducing an aqueous dilute solution of sodium hydroxide. The reaction mixture is heated further to 150° C. and stirred at this temperature for about 30 minutes until the evolution of hydrogen chloride has ceased. The melt of the reaction mixture is poured into water. After filtration and comminution, 72.4 parts of the compound of formula (15) as indicated in Example 7 are obtained as a pale pink powder. Melting point: 62°–68° C. Acid number: 151.

APPLICATION EXAMPLES

Examples 23 to 48

To a fibre suspension which contains bleached birch sulfate pulp and pine sulfate pulp in a weight ratio of 1:1 in water of 10° (German water hardness), and which has a Schopper-Riegler freeness of 35° and a solids content of 0.5%, are added 20% of chalk as filler and then 0.01% of PERCOL® 292 (cationic high molecular weight (MG>1.10$^7$) polyacrylamide) as auxiliary for retaining pulp fibre microparticles. The pH of the fibre suspension is as indicated in Table I below. The percentages refer to solids in filler and assistant, based on the solids content of the fibre suspension.

Formulations of the sizing agent are prepared by stirring 7% of each of the indicated sizing agents in powder form (obtained as crude product) with 3.5% of POLYMIN® P (polyethylenimine with a molecular weight of 10,000 to 100,000) as retention aid, in the presence of deionised water and of glass beads having a diameter 2 mm, at room temperature (15° to 25° C). The dispersions so obtained are pourable, homogeneous and storage stable. The percentages refer to solids in fillers and retention aids, based on the total weight of the formulation.

The aqueous formulation of the sizing agent and the retention aid is then added to the fibre suspension in such a manner as to give 0.5% solids content of sizing agent, based on the solids content of the fibre suspension. The fibre suspension is then processed in a laboratory "Formette Dynamique" sheet former (supplied by Allimand, Grenoble, France) to paper sheets which, after they have been dried at 130° C. for 3 minutes, have a weight per unit area of 80 g/m$^2$.

Both surfaces of the paper sheets so obtained, i.e. the surface obtained on the wire side of the sheet former and the adjacent or top side, are tested for their sizing properties. This is done by measuring the water absorption according to Cobb over 30 seconds (WA Cobb$_{30}$) in accordance with DIN 53 132. The results of the WA Cobb$_{30}$ measurements in g/m$^2$ of the wire side (WS) and top side (TS) after drying at 130° C. and storage for 1 day at 23° C. and 50% relative humidity are reported in Table I. The lower the water absorption, the better the paper sizing. WA Cobb$_{30}$ values above 100 denote a completely unsatisfactory sizing of the paper.

TABLE I

| Ex. | Sizing agent | pH of the fibre suspension | WA Cobb$_{30}$ (g/m$^2$) after drying WS | after drying TS | after storage for 1 day WS | after storage for 1 day TS |
|---|---|---|---|---|---|---|
| 23 | Compound of Example A | 8.7 | 23 | 14 | 24 | 14 |
| 24 | Compound of Example B | 8.7 | 17 | 13 | 17 | 14 |
| 25 | Compound of Example D | 8.5 | 21 | 16 | 24 | 17 |
| 26 | Compound of Example E | 8.2 | 56 | 20 | 21 | 12 |
| 27 | Compound of Example G | 9.3 | 69 | 19 | 40 | 15 |
| 28 | Compound of step 2 of Example I | 8.1 | 19 | 14 | 18 | 11 |
| 29 | Compound of Example J | 8.7 | 52 | 14 | 20 | 12 |
| 30 | Compound of Example 1 | 8.7 | 17 | 13 | 18 | 14 |
| 31 | Compound of Example 2 | 8.7 | 47 | 18 | 43 | 15 |
| 32 | Compound of Example 3 | 7.9 | 20 | 15 | 19 | 16 |
| 33 | Compound of Example 4 | 7.9 | 17 | 14 | 16 | 13 |
| 34 | Compound of Example 7 | 7.9 | 16 | 14 | 16 | 12 |
| 35 | Compound of Example 8 | 9.2 | 32 | 15 | 27 | 12 |
| 36 | Compound of Example 9 | 9.2 | 35 | 15 | 30 | 12 |
| 37 | Compound of Example 10* | 8.2 | 31 | 16 | 18 | 12 |
| 38 | Compound of Example 11 | 8.4 | 66 | 16 | 42 | 12 |
| 39 | Compound of Example 13 | 9.4 | 25 | 13 | 19 | 13 |
| 40 | Compound of Example 14 | 8.7 | 44 | 14 | 26 | 12 |
| 41 | Compound of Example 15 | 8.7 | 24 | 14 | 25 | 13 |
| 42 | Compound of Example 16 | 8.2 | 26 | 15 | 26 | 14 |
| 43 | Compound of Example 17 | 9.0 | 20 | 14 | 19 | 12 |
| 44 | Compound of Example 18 | 9.1 | 26 | 15 | 22 | 13 |
| 45 | Compound of Example 19** | 9.1 | 38 | 18 | 18 | 13 |
| 46 | Compound of Example 20 | 8.7 | 22 | 11 | 15 | 11 |
| 47 | Compound of Example 21 | 8.8 | 32 | 13 | 32 | 12 |

TABLE I-continued

| Ex. | Sizing agent | pH of the fibre suspension | WA Cobb$_{30}$ (g/m$^2$) after drying WS | TS | after storage for 1 day WS | TS |
|---|---|---|---|---|---|---|
| 48 | Compound of Example 22*** | 8.3 | 21 | 12 | 20 | 9 |

*formulation in the presence of 0.35% of sodium lauryl sulfate (in addition to 7% of sizing agent and 3.5% of POLYMIN ® P)
**formulation as melt emulsion in the presence of 0.35% of sodium lauryl sulfate (in addition to 7% of sizing agent in the melt state and 3.5% of POLYMIN ® P)
***formulation with an aqueous solution of acetic acid, adjusted to pH 7.0

Similar results are obtained by replacing POLYMIN ® P as cationic retention aid with CATO ® 110 (cationically modified starch which is modified with a propylene oxide containing ammonium groups; pH of a 25% suspension in distilled water at 20° C.=4.2 to 4.6), POSAMYL ® E7 (cationically modified starch with a nitrogen content of 0.4%), HOFFMANN ® B 118 (native potato starch cationically modified with trimethylglycidylasssonium chloride and having a nitrogen content of 1.3%), a condensate of dicyandiamide and triethylenetetramine which is further reacted with epichlorohydrin and is prepared in accordance with Example 2 of "German Offenlegungsschrift" No. 2,710,061, an adduct of epichlorohydrin and a reaction product of diethylenediamine and adipic acid, prepared in accordance with Example 1 of British Patent No. 865,727, a reaction product of dicyandiamide, formaldehyde, ammonium chloride and ethylenediamine, prepared in accordance with Example 1 of U.S. Pat. No. 3,491,064, or RETAMINOL ® K (polyethylenimine of mol wt 20,000 to 40,000). Mixtures of the retention aids of the above indicated kind are also suitable. To obtain good results, it can be advantageous to add dispersants, in particular condensates of formaldehyde and naphthalenesulfonic acids, or carboxymethyl cellulose. However, only a poor sizing with Cobb values of about 150 to 200 are obtained by using a sizing agent of Example A, B, D, E, G, I, J or of any one of Examples 1 to 4, 7 to 11 or 13 to 22, but without retention aid, or a retention aid of the above indicated kind but without a sizing agent.

Examples 49 to 60

The procedures of Examples 23 to 48 are repeated, except that the sizing agent and retention aid are added separately to the fibre suspension. The sizing agent (6, 7, 10 or 15%) is stirred, in powder form, at room temperature (15°-25° C.), in the presence of water and glass beads, with an aqueous 5% ammonia solution to give a self-emulsifying, pourable and storage stable emulsion, which can be further diluted, of the sizing agent formulations as indicated in Table II. If desired, it is also possible to add direct salt-containing, self-emulsifiying, pourable and storage stable emulsions of the sizing agent as obtained in the synthesis, without the addition of ammonia. The val % indicates the number of equivalents of ammonia for 100 equivalents, based on the number of acidic groups contained in the respective sizing agent. The indicated amount of the retention aid POLYMIN ®, expressed as solids, is added to the fibre suspension 10 seconds after the addition of the indicated amount of sizing agent, expressed as solids, said amounts being based on the solids content of the fibre suspension. The sizing results are also reported in Table II.

TABLE II

| Ex. | Formulation of the sizing agent | Amount of the sizing agent (%) | Amount of retention-aid (%) | pH of the suspension | WA Cobb$_{30}$ (g/m$^2$) after drying WS | TS | after storage for 1 day TS | SS |
|---|---|---|---|---|---|---|---|---|
| 49 | 15% of the compound of Example B 60 val % of ammonia | 0.30 | 0.25 | 8.8 | 18 | 15 | 19 | 14 |
| 50 | 15% of the compound of Example C 100 val % of ammonia | 0.50 | 0.25 | 8.1 | 33 | 23 | — | — |
| 51 | 15% of the compound of Example D 100 val % of ammonia | 0.50 | 0.25 | 8.5 | 21 | 16 | 24 | 17 |
| 52 | 10% of the compound of Example F * | 0.50 | 0.25 | 8.5 | 21 | 18 | 25 | 19 |
| 53 | 10% of the compound of Example H | 0.50 | 0.25 | 8.6 | 36 | 36 | — | — |
| 54 | 15% of the compound of Example 1 60 val % of ammonia | 0.30 | 0.25 | 8.8 | 18 | 15 | 19 | 14 |
| 55 | 10% of the compound of Example 4 100 val % of ammonia | 0.15 | 0.15 | 8.4 | 27 | 20 | 22 | 19 |
| 56 | 10% of the compound of Example 5 100 val % of ammonia | 0.15 | 0.15 | 8.6 | 27 | 24 | 23 | 20 |
| 57 | 10% of the compound of Example 6 100 val % of ammonia | 0.15 | 0.15 | 8.3 | 30 | 25 | 28 | 23 |
| 58 | 10% of the compound of Example 7** 100 val % of ammonia | 0.15 | 0.15 | 8.5 | 25 | 23 | 22 | 20 |
| 59 | 7% of the compound | 0.50 | 0.25 | 9.3 | 29 | 29 | 30 | 26 |

TABLE II-continued

| Ex. | Formulation of the sizing agent | Amount of the sizing agent (%) | Amount of retention-aid (%) | pH of the suspension | WA Cobb$_{30}$ (g/m$^2$) after drying WS | WA Cobb$_{30}$ (g/m$^2$) after drying TS | WA Cobb$_{30}$ (g/m$^2$) after storage for 1 day TS | WA Cobb$_{30}$ (g/m$^2$) after storage for 1 day SS |
|---|---|---|---|---|---|---|---|---|
| 60 | of Example 12 100 val % of ammonia 6% of the compound of Example 22** 100 val % of ammonia | 0.50 | 0.25 | 8.2 | 17 | 12 | 15 | 10 |

\* as 10% suspension containing ammonium chloride and without addition of ammonia
\*\* in the presence of 0.5 of lignincarboxylate as dispersing assistant Sizing results analogous to those reported in Table II are obtained by using from 10 to 200 val % of ammonia or sodium hydroxide (as 5% aqueous solutions) for formulating the sizing agent.

Similar results are also obtained by first adding the retention aid to the fibre suspension and subsequently adding the sizing agent 10 seconds later. The same also applies by dispensing with the addition of PERCOL ® 292 and/or of a filler. Similar results are likewise obtained by using talcum or kaolin as filler instead of chalk or by additionally using alum. Good sizing results are also obtained by using fibre suspensions which contain groundwood.

Example 61

A pure cellulose filter paper with a weight per unit area of 110 g/m$^2$ is padded at a rate of 3 m/minute and a roller pressure of 20 kp/cm with an aqueous liquor which contains 18.4 g of an aqueous dispersion of 7% of the compound of Example 22 as sizing agent and 3.5% of POLYMIN ® P as retention aid and which has been adjusted to pH 7.0 with an aqueous solution of acetic acid. The dispersion of the sizing agent and of the retention aid is prepared as described in Examples 23 to 48.

The pick-up is 78% (0.1% of pure sizing agent, based on the paper to be treated). The padded paper is dried between two sheets of filter paper for 3 minutes at 90° C. The dried, treated paper has a WA Cobb$_{30}$ value of 19 /m$^2$. After storage for 1 day, the WA Cobb$_{30}$ value of the treated paper is 16 g/m$^2$. Similar results are also obtained by using dispersions or melt emulsions which contain, as sizing agent, a compound of any one of Examples H to J or of any one of Examples 1 to 21 instead of the compound of Example 22.

What is claimed is:

1. A process for sizing paper or cardboard which comprises treating the fibers thereof with
(A) a sizing agent of the formula $$A_1-D_1-(CH_2)_{n-1}-X_1-R_1$$
$$|$$
$$(A_2)_{m-1}$$

wherein
$A_1$ and $A_2$ are each an anionic carboxyl, hydroxyl or sulfo group which is acidic or in salt form,
$D_1$ is phenylene, naphthylene, dihydronaphthylene or tetrahydronaphthylene, each of which is unsubstituted or substituted by halogen, nitro, amino or hydroxyl,
$R_1$ is alkyl or alkenyl, each of 5 to 22 carbon atoms,
$X_1$ is a bridge of the formula —O—CO—, wherein the terminal —CO— group of said bridge is attached to the alkyl or alkenyl radical $R_1$, and
m and n are each 1 or 2, and
(B) a polyethyleneimine retention aid.

2. A process according to claim 1 for mass sizing paper or cardboard, which comprises adding components (A) and (B), in either order or simultaneously, to an aqueous cellulose-containing fiber suspension which optionally contains filler.

3. A process according to claim 1 for surface sizing paper, which comprises impregnating said paper with an aqueous sizing liquor which contains components (A) and (B) drying said paper.

4. A process according to claim 1, wherein the retention aid (B) has a molecular weight of 1000 to 2,000,000.

5. A process according to claim 2, which comprises using 0.02 to 3 percent by weight of the sizing agent (A) and 0.02 to 3 percent by weight of the retention aid (B), both amounts being expressed as solids in (A) and (B) and based on the solids content of the fibre suspension.

6. A process according to claim 2, which comprises using, as optional filler, a condensate of formaldehyde and urea, titanium dioxide, talcum, kaolin, montmorillonite or chalk.

7. A process according to claim 2, wherein the fiber suspension has a Schopper-Riegler freeness of 10° to 60° and a solids content of 0.1 to 5 percent by weight.

8. A process according to claim 2, wherein the fiber suspension contains sulfite and/or sulfate pulp obtained from coniferous and/or hardwood, optionally groundwood and/or alum containing waste paper.

9. A process according to claim 3, wherein the paper is dried in the temperature range from 60° to 140° C.

10. A process according to claim 1, wherein
$D_1$ is phenylene or naphthylene, each unsubstituted or substituted by chlorine, bromine, nitro, amino or hydroxyl,
m is 1 and
n is 1 or 2, $X_1$ is —O—CO— and $R_1$ is alkyl or alkenyl, each of 5 to 21 carbon atoms.

11. A process according to claim 1, which comprises using, as component (A), a sizing agent of the formula

[chemical structure: benzene ring with $A_1$ substituent, $(HO)_{m-1}$ substituent, and $X_2-C(=O)-R_4$ substituent]

[chemical structure: naphthalene ring with $A_1$ substituent, $(OH)_{n-1}$ substituent, and $X_2-C(=O)-R_4$ substituent]

wherein $R_4$ is alkyl or alkenyl, each of 15 to 21 carbon atoms, and $X_2$ is —O—.

* * * * *